United States Patent
Jang et al.

(10) Patent No.: US 10,167,424 B2
(45) Date of Patent: Jan. 1, 2019

(54) COLOR-TUNABLE UP-CONVERSION NANOPHOSPHOR

(71) Applicant: Korea Institute of Science and Technology, Seoul (KR)

(72) Inventors: Ho Seong Jang, Seoul (KR); Joon Soo Han, Seoul (KR); So Hye Cho, Seoul (KR); Seung Yong Lee, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 15/364,431

(22) Filed: Nov. 30, 2016

(65) Prior Publication Data

US 2018/0016497 A1     Jan. 18, 2018

(51) Int. Cl.

| | | |
|---|---|---|
| *C09K 11/77* | (2006.01) | |
| *A61K 49/00* | (2006.01) | |
| *C09K 11/02* | (2006.01) | |
| *G01N 21/64* | (2006.01) | |
| *G07D 7/12* | (2016.01) | |
| *H01L 31/055* | (2014.01) | |
| *B82Y 5/00* | (2011.01) | |

(52) U.S. Cl.
CPC ...... *C09K 11/7773* (2013.01); *A61K 49/0019* (2013.01); *A61K 49/0065* (2013.01); *C09K 11/025* (2013.01); *C09K 11/7705* (2013.01); *C09K 11/7791* (2013.01); *G01N 21/6428* (2013.01); *G07D 7/122* (2013.01); *H01L 31/055* (2013.01); *B82Y 5/00* (2013.01); *G01N 2021/6439* (2013.01)

(58) Field of Classification Search
CPC combination set(s) only.
See application file for complete search history.

(56) References Cited

U.S. PATENT DOCUMENTS

2015/0182641 A1\*    7/2015   Tan .................... A61K 49/0002
                                                                424/9.32

OTHER PUBLICATIONS

Mahalingann et al., Adv. Mater. 2009, 21, 4025-4028 (Year: 2009).\*

\* cited by examiner

*Primary Examiner* — Robert S Cabral
(74) *Attorney, Agent, or Firm* — NSIP Law

(57) ABSTRACT

Provided are a nanophosphor and a silica composite including the nanophosphor. The nanophosphor has a core/first shell/second shell structure or a core/first shell/second shell/third shell structure, wherein the core includes a $Yb^{3+}$-doped fluoride-based nanoparticle, the first shell is an up-conversion shell including a $Yb^{3+}$ and $Tm^{3+}$-codoped fluoride-based crystalline composition, the second shell is a fluoride-based emission shell, and the third shell is an outermost crystalline shell.

11 Claims, 8 Drawing Sheets

COLOR-TUNABLE UP-CONVERSION NANOPHOSPHOR

CROSS-REFERENCE TO RELATED APPLICATION

This application claims the benefit of Korean Patent Application No. 10-2016-0088780, filed on Jul. 13, 2016, in the Korean Intellectual Property Office, the disclosure of which is incorporated herein in its entirety by reference.

BACKGROUND

1. Field

The present invention relates to a nanophosphor that is applicable to anti-falsification, fluorescent contrast media, and transparent display and a method of synthesizing the same, and in particular, to a fluoride-based core/first shell/second shell/third shell nanophosphor that has a particle size of about 1 to about 50 nm, emits visible light when excited by infrared light, and has a tetragonal structure, wherein the nanophosphor emits blue, green, red, or white light due to energy transition between a core and a shell and energy transition among sensitizers constituting shell layers.

2. Description of the Related Art

Nanophosphor includes an inorganic host having a size of 100 nm or less and lanthanide doped thereon. In the case of a nanophosphor doped with a trivalent lanthanide ion, its emission color depends on the doped lanthanide, not its host. This is because the emission of the nanophosphor occurs due to $4f$-$4f$ electron transition within the trivalent lanthanide ion doped on the host. Since electrons of the $4f$ orbital are located inner than $5s$ and $5p$ orbitals, the electrons are relatively less affected by external impacts, and even when lanthanide is doped on different hosts, light having a unique wavelength corresponding to the lanthanide may be emitted. Accordingly, unlike quantum dots, of which emission characteristics vary according to the size of particles, even with non-homogenous particle sizes, desired emission wavelengths may be maintained.

As for most phosphors including nanophosphors, when high-energy light, such as ultraviolet light or visible light, is radiated to a phosphor, an electron may transition from a ground energy level, and then, energy loss may occur, and visible light, having a wavelength longer than that of incident light, may be emitted. The difference between an absorption wavelength and an emission wavelength is referred to as stokes shift. In this regard, when some lanthanides are doped, electrons may be excited due to infrared light, and visible light, which has a shorter wavelength, that is, a higher energy level than exiting light, may be emitted: anti-stokes shift. This is referred to as up-conversion emission, which is distinguishable from down-conversion in which emission energy is lower than excitation energy. Phosphors showing up-conversion emission emit light when exposed to infrared light. Accordingly, such phosphors are suitable for use as fluorescent contrast media. This is because since, during cell imaging, the use of infrared light does not induce self-emission in cells, up-conversion phosphors may provide fluorescent images having a high signal-to-noise ratio. Unlike commercially available powder micro-phosphors, nanophosphors having a nanometer region may attach on the surface of cells or enter into cells. Accordingly, such nanophosphors are applicable to bio-imaging, such as cell imaging or in-vivo imaging. For use as contrast media for bio images, organic dyes are widely used. Organic dyes emit various colors of light having strong emission intensities. However, they have very weak photostability, and accordingly, even when the light-exposure time increases slightly, emission intensities are substantially decreased. This feature can be overcome by using an inorganic emission material, for example, quantum dots, as contrast media for bio images. In this case, however, quantum dots may cause flickering emission, and like CdSe, when heavy metal, such as Cd, is included, their applicability may be decreased.

In the case of nanophosphors, since nanophosphors are an inorganic material, excellent photostability may be obtained. Also, due to the absence of a toxic element, such as Cd, nanophosphors are an excellent alternative to fluorescent contrast media of the related art. However, up-conversion emission shows low emission efficiency, since after two photons having small energy are absorbed by phosphor, one photon having an energy intensity greater than the other emits light. In particular, in the case of a phosphor having a relatively small particle size, that is, a nanophosphor, surface defects may be serious per unit volume, leading to further lower up-conversion emission efficiency. Accordingly, for high-sensitivity fluorescent imaging, there is a need to develop a nanophosphor having a small, uniform particle size and strong up-conversion emission intensity. Conventionally, up-conversion emission effectively occurs in Tm, Er, and Ho. Accordingly, it is difficult to produce light having a wavelength region other than those of Tm, Er, and Ho. However, if an up-conversion nanophosphor that can emit light having a wavelength region other than those of Tm, Er, and Ho when exposed to infrared light as an exciting light source is developed, such an up-conversion nanophosphor may be applicable to bio imaging, such as multiplexing imaging, and imaging accuracy may be further improved. In addition, when the up-conversion nanophosphor emits various colors of visible light when exposed to a single infrared ray wavelength of light, it is applicable to transparent displays. Furthermore, since color other than the color embodied by Tm, Er, and Ho can be obtained, when the up-conversion nanophosphor is used for security applications using infrared rays, a security level may be increased.

SUMMARY

Provided is an up-conversion nanophosphor having, as a host, $LiGdF_4$ having a single tetragonal structure having a scheelite structure, which is known to have high emission efficiency, wherein the $LiGdF_4$ is doped with Tm, Tb, and Eu to produce various colors of light. In detail, to embody a strong up-conversion emission, a core/first shell/second shell/third shell structure is introduced, the location where a sensitizer is doped is limited to shell layers, and the concentration of the sensitizer is controlled to emit various color of light. Also, the concentration of the co-sensitizer is controlled to emit white light. However, these embodiments are presented herein for illustrative purpose only, and the scope of the present disclosure is not limited thereto.

Additional aspects will be set forth in part in the description which follows and, in part, will be apparent from the description, or may be learned by practice of the presented embodiments.

According to an aspect of an embodiment, a nanophosphor includes an $Yb^{3+}$-doped fluoride-based nanoparticle represented by Formula 1:

$$LiY_{1-x-y}L_yF_4:Yb^{3+}_x.$$ 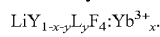

In Formula 1, x satisfies the condition of $0 \leq x \leq 1$ and is a real number; y satisfies the condition of $0 \leq y \leq 1$, is a real number, satisfies the condition of $0 \leq x+y \leq 1$, and may be any real number that satisfies the condition of $x+y \leq 1$; and L may be any one selected from Y, Dy, Ho, Er, Tm, Lu, and a combination thereof.

The nanophosphor may include a core including the nanoparticle and a shell located on the surface of the core, and the shell may include a compound represented by Formula 2:

$$LiGd_{1-p-q-r}M_rF_4:Yb^{3+}{}_p,Tm^{3+}{}_q. \quad \text{[Formula 2]}$$

In Formula 2, p satisfies the condition of $0 < p \leq 0.5$ and is a real number, and q satisfies the condition of $0 < q \leq 0.2$ and is a real number.

In Formula 2, r satisfies the condition of $0 \leq r \leq 1$ and is a real number, r may be any real number that satisfies the condition of $0 < p+q+r < 1$, and M may be any one selected from a rare-earth element and a combination thereof.

The rare-earth element may be any one selected from Gd, Y, La, Ce, Pr, Nd, Pm, Sm, Eu, Tb, Dy, Ho, Er, and Lu.

The nanophosphor may include the core and the shell, and $Yb^{3+}$, which is a co-sensitizer, absorbs infrared light and transfers the absorption energy to $Tm^{3+}$, resulting in emission peaks in an ultraviolet light region and a blue light region.

The nanophosphor may include the nanoparticle-including core/first shell and a second shell located on the surface of the core/first shell, and the second shell may include a compound represented by Formula 3:

$$LiGd_{1-s-t-u}N_uF_4:Tb^{3+}{}_s,Eu^{3+}{}_t. \quad \text{[Formula 3]}$$

In Formula 3, s satisfies the condition of $0 < s \leq 0.5$ and is a real number, and t satisfies the condition of $0 < t \leq 0.5$ and is a real number.

In Formula 3, u satisfies the condition of $0 \leq u \leq 1$ and is a real number, u may be any real number that satisfies the condition of $0 < s+t+u < 1$, and N may be any one selected from a rare-earth element and a combination thereof.

The rare-earth element may be any one selected from Gd, Y, La, Ce, Pr, Nd, Pm, Sm, Dy, Ho, Er, Tm, Yb, and Lu.

The nanophosphor may include the nanoparticle-containing core/first shell/second shell, and a third shell located on the surface of the core/first shell/second shell, and the third shell may include a compound represented by Formula 4:

$$LiY_{1-v}O_vF_4. \quad \text{[Formula 4]}$$

In Formula 4, v satisfies the condition of $0 \leq v \leq 1$ and is a real number, and O may be any one selected from a rare-earth element and a combination thereof.

The rare-earth element may be any one selected from Y, La, Ce, Pr, Nd, Pm, Sm, Eu, Gd, Tb, Dy, Ho, Er, Tm, Yb, and Lu.

The nanoparticle may have a size of about 2 nm to about 70 nm.

The nanoparticle may have up-conversion characteristics.

BRIEF DESCRIPTION OF THE DRAWINGS

Embodiments of the inventive concept will be more clearly understood from the following detailed description taken in conjunction with the accompanying drawings in which.

DETAILED DESCRIPTION

Figure 1:
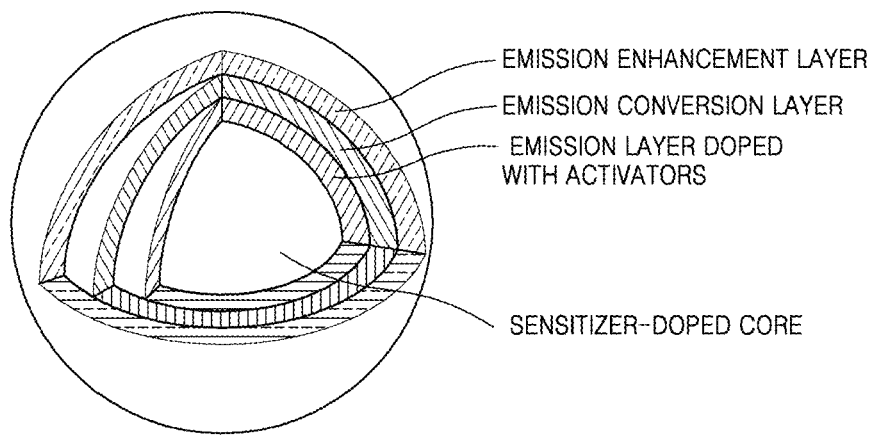
FIG. 1 shows a conceptual view of a nanophosphor having a core/first shell/second shell/third shell structure according to an embodiment of the present disclosure.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. For ease of description, in the drawings, the sizes of at least some elements are exaggerated for clarity. Like reference numbers in the drawings denote like elements.

Hereinafter, with reference to the attached drawings, a color-tunable core/first shell/second shell/third shell structure according to embodiments of the present disclosure will be described. The core/first shell/second shell/third shell structure may include a $LiY_{1-x-y}L_yF_4:Yb^{3+}_x/LiGd_{1-p-q-r}M_rF_4:Yb^{3+}_p,Tm^{3+}_q/LiGd_{1-s-t-u}N_uF_4:Tb^{3+}_s,Eu^{3+}_t/LiY_{1-v}O_vF_4$ structure. Regarding this structure, x satisfies the condition of 0≤x≤1 and is a real number; y satisfies the condition of 0≤y≤1, is a real number, satisfies the condition of 0≤x+y≤1, and may be any real number that satisfies the condition of x+y≤1; and L may be any one selected from Y, Dy, Ho, Er, Tm, Lu, and a combination thereof; p satisfies the condition of 0<p≤0.5 and is a real number, q satisfies the condition of 0<q≤0.2 and is a real number, r satisfies the condition of 0≤r≤1 and is a real number, r may be any real number that satisfies the condition of 0<p+q+r<1, and M may be any one selected from a rare-earth element and a combination thereof; s satisfies the condition of 0<s≤0.5 and is a real number, t satisfies the condition of 0<t≤0.5 and is a real number, u satisfies the condition of 0≤u≤1 and is a real number, u may be any real number that satisfies the condition of 0<s+t+u<1, and N may be any one selected from a rare-earth element and a combination thereof; and v satisfies the condition of 0≤v≤1 and is a real number, and O may be any one selected from a rare-earth element and a combination thereof. Hereinafter, up-conversion nanophosphors will be described. However, the concept of the present disclosure is not limited to embodiments to be presented below, and other embodiments may also be provided by, for example, the addition or substitution of constituting elements.

Embodiments explained in connection with the drawings are not interpreted as limiting the concept of the present disclosure, and shall be considered as to fully explain the present disclosure.

Hereinafter, examples of a method of preparing an up-conversion/down-conversion double emission fluoride-based nanophosphor having a core/first shell/second shell/third shell structure will be described.

<Comparative Example 1> Preparation of 0.25 mmol $Yb^{3+}$ and 0.01 mmol $Tm^{3+}$-Doped Up-Conversion Core Nanophosphor 0.74 mmol gadolinium chloride hexahydrate ($GdCl_3.6H_2O$), 0.25 mmol ytterbium chloride hexahydrate ($YbCl_3.6H_2O$), 0.01 mmol thulium chloride hexahydrate ($TmCl_3.6H_2O$), and 3.1 mmol oleic acid sodium ($C_{18}H_{33}O_2Na$) were estimated, and a mixed solvent including water, ethanol, and hexane was added thereto in a predetermined amount. The mixture was heat-treated at a temperature of 70° C. to form a lanthanide complex compound (step of preparing a complex compound). The complex compound was mixed with a solution including an oleic acid and 1-octadecene, and then, heat-treated at a temperature of 150° C. for 30 minutes to prepare a mixed solution including the lanthanide complex compound (step of preparing a first mixed solution).

10 ml of a methanol solution including 2.5 mmol lithium hydroxide and 4 mmol ammonium fluoride was prepared (step of preparing a second mixed solution) and then mixed with the mixed solution including the lanthanide complex compound (step of preparing a reaction solution).

The resultant mixed solution was sufficiently mixed, and then, methanol was removed therefrom, followed by heat-treatment in inert gas atmosphere. In this regard, when the heat-treatment temperature is less than 200° C., single tetragonal nanocrystals are not completely formed, and thus, the formed phosphor may not have strong emission characteristics; and when the heat-treatment temperature exceeds 370° C., over-reaction may occur, and thus, particles may agglomerate together to form larger particles, and the size distribution of formed particles is not uniform, leading to low luminance. Accordingly, the heat-treatment temperature was controlled to be in a range of 200 to 370° C., and the heat-treatment time was controlled to be in a range of 10 minutes to 4 hours (step of forming a nanoparticle). After the heat-treatment, the result was cooled to room temperature, thereby producing nanophosphor in the colloid state, having a particle diameter of 1 nm to 40 nm. The nanophosphor was washed with acetone or ethanol, and then, for storage purpose, dispersed in a non-polar solvent, for example, hexane, toluene, chloroform, or like.

<Example 1> Preparation of 0.8 mmol $Yb^{3+}$-Doped Up-Conversion Core Nanophosphor 0.2 mmol yttrium chloride hexahydrate ($YCl_3.6H_2O$), 0.8 mmol ytterbium chloride hexahydrate ($YbCl_3.6H_2O$), and 3.1 mmol oleic acid sodium ($C_{18}H_{33}O_2Na$) were estimated, and a mixed solvent including water, ethanol, and hexane was added thereto in a predetermined amount. The mixture was heat-treated at a temperature of 70° C. to form a lanthanide complex compound (step of preparing a complex compound). The complex compound was mixed with a solution including an oleic acid and 1-octadecene, and then, heat-treated at a temperature of 150° C. for 30 minutes to prepare a first mixed solution including the lanthanide complex compound (step of preparing a first mixed solution).

10 ml of a methanol solution including 2.5 mmol lithium hydroxide and 4 mmol ammonium fluoride was prepared (step of preparing a second mixed solution), and then mixed with the first mixed solution including the lanthanide complex compound (step of preparing a reaction solution).

The resultant mixed solution was sufficiently mixed, and then, methanol was removed therefrom, followed by heat-treatment in inert gas atmosphere. In this regard, when the heat-treatment temperature is less than 200° C., single tetragonal nanocrystals are not completely formed, and thus, the formed phosphor may not have strong emission characteristics; and when the heat-treatment temperature exceeds 370° C., over-reaction may occur, and thus, particles may agglomerate together to form larger particles, and the size distribution of formed particles is not uniform, leading to low luminance. Accordingly, the heat-treatment temperature was controlled to be in a range of 200 to 370° C., and the heat-treatment time was controlled to be in a range of 10 minutes to 4 hours (step of forming a nanoparticle). After the heat-treatment, the result was cooled to room temperature, thereby producing nanophosphor in the colloid state, having a particle diameter of 1 nm to 40 nm. The nanophosphor prepared according to Example 1 included $LiY_{0.2}F_4:Yb^{3+}_{0.8}$ nanoparticle. The nanophosphor was washed with acetone or ethanol, and then, for storage purpose, dispersed in a non-polar solvent, for example, hexane, toluene, chloroform, or like.

<Example 2> Preparation of Up-Conversion Nanophosphor Having Core/First Shell Structure by Using $Yb^{3+}$ and $Tm^{3+}$-Codoped Fluoride Shell A nanophosphor having a core/first shell structure was prepared by using the $LiY_{0.2}F_4:Yb^{3+}_{0.8}$ nanoparticle prepared according to Example 1, which is a core, and a $Yb^{3+}$ and $Tm^{3+}$-codoped fluoride-based compound.

0.74 mmol gadolinium chloride hexahydrate ($GdCl_3 \cdot 6H_2O$), 0.25 mmol ytterbium chloride hexahydrate ($YbCl_3 \cdot 6H_2O$), and 0.01 mmol thulium chloride hexahydrate ($TmCl_3 \cdot 6H_2O$) were mixed with a solution including an oleic acid and 1-octadecene, and the resultant mixture was heat-treated at a temperature of 150° C. for 30 minutes to prepare a mixed solution including a lanthanide complex compound (step of preparing a first mixed solution).

The first mixed solution was mixed with a solution including the $LiY_{0.2}F_4:Yb^{3+}_{0.8}$ nanoparticle prepared according to Example 1 to prepare a second mixed solution.

10 ml of a methanol solution including 2.5 mmol lithium hydroxide and 4 mmol ammonium fluoride was prepared (step of preparing a third mixed solution), and then mixed with the second mixed solution including the lanthanide complex compound (step of preparing a reaction solution).

The resultant mixed solution was sufficiently mixed, and then, methanol was removed therefrom, followed by heat-treatment in inert gas atmosphere. In this regard, when the heat-treatment temperature is less than 200° C., single tetragonal nanocrystals are not completely formed, and thus, the formed phosphor may not have strong emission characteristics; and when the heat-treatment temperature exceeds 370° C., over-reaction may occur, and thus, particles may agglomerate together to form larger particles, and the size distribution of formed particles is not uniform, leading to low luminance. Accordingly, the heat-treatment temperature was controlled to be in a range of 200 to 370° C., and the heat-treatment time was controlled to be in a range of 10 minutes to 4 hours (step of forming a nanoparticle). After the heat-treatment, the result was cooled to room temperature, thereby producing nanophosphor in the colloid state, having a particle diameter of 1 nm to 30 nm. The nanophosphor prepared according to Example 2 included the $LiY_{0.2}F_4:Yb^{3+}_{0.8}$ core prepared according to Example 1 and a $LiGdF_4:Yb^{3+}_{0.25},Tm^{3+}_{0.01}$ shell. The nanophosphor was washed with acetone or ethanol, and then, for storage purpose, dispersed in a non-polar solvent, for example, hexane, toluene, chloroform, or like.

Figure 2:
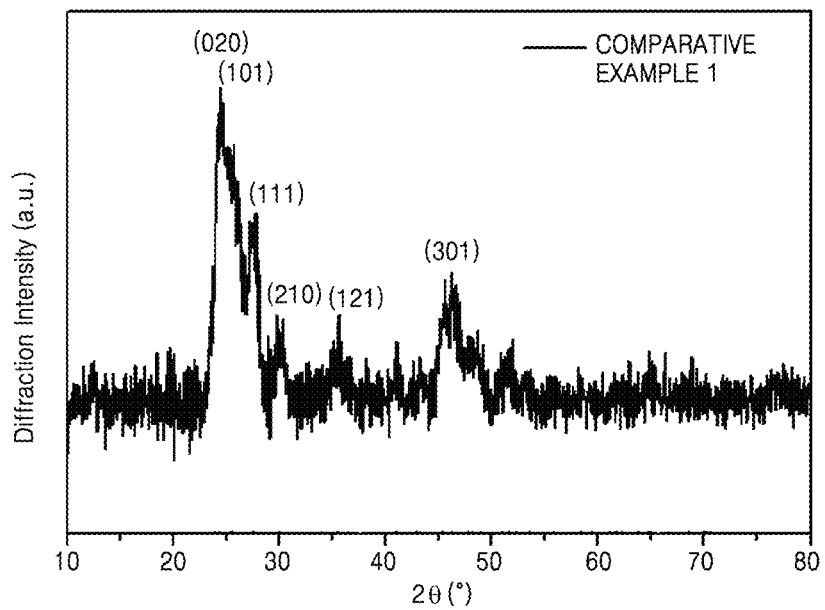
FIG. 2 shows an X-ray diffraction pattern showing a core up-conversion nanophosphor prepared according to Comparative Example.
Figure 3:
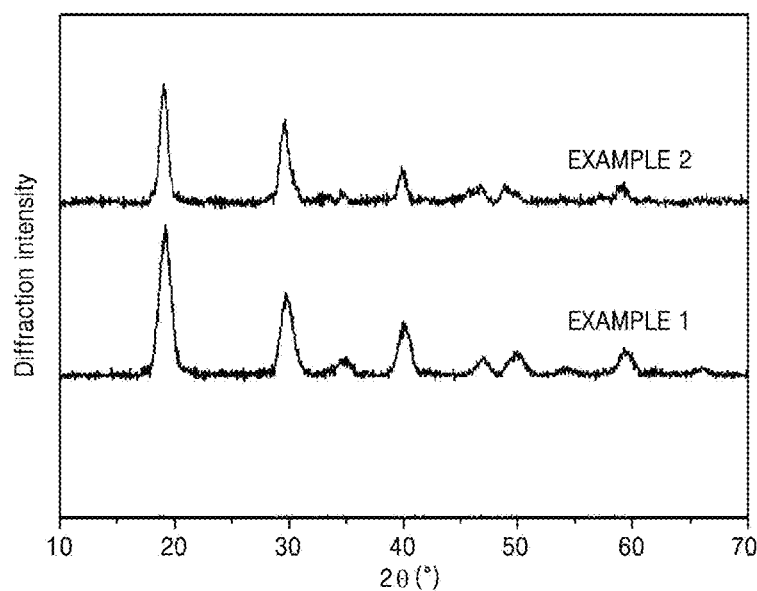
FIG. 3 shows X-ray diffraction patterns of a nanophosphor including a core prepared according to Example 1 and a nanophosphor including a core/first shell structure prepared according to Example 2.

FIG. 1 shows a conceptual view of a nanophosphor having a core/first shell/second shell/third shell structure according to an embodiment of the present disclosure. FIG. 2 shows an X-ray diffraction pattern showing a core up-conversion nanophosphor prepared according to Comparative Example 1. FIG. 3 shows X-ray diffraction patterns of an up-conversion nanophosphor including a core synthesized according to Example 1 and an up-conversion nanophosphor including a core/first shell structure synthesized according to Example 2.

In a nanophosphor having a core/first shell/second shell/third shell structure according to an embodiment, the core corresponds to the 'sensitizer-doped core' illustrated in FIG. 1, the first shell corresponds to the 'emission layer doped with activators' illustrated in FIG. 1, the second shell corresponds to the 'emission conversion layer illustrated in FIG. 1, and the third shell corresponds to the 'emission enhancement layer' illustrated in FIG. 1.

Figure 4:
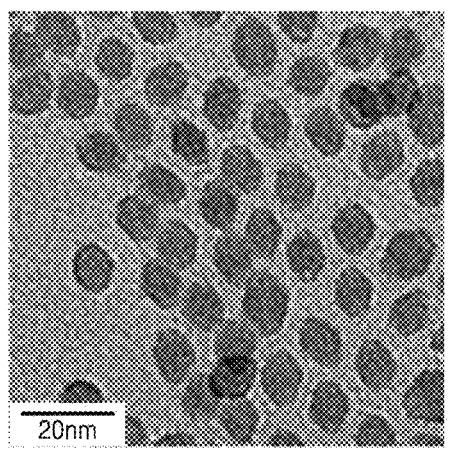
FIG. 4 shows a transmission electron microscopic image of a core nanoparticle according to an embodiment.
Figure 5:
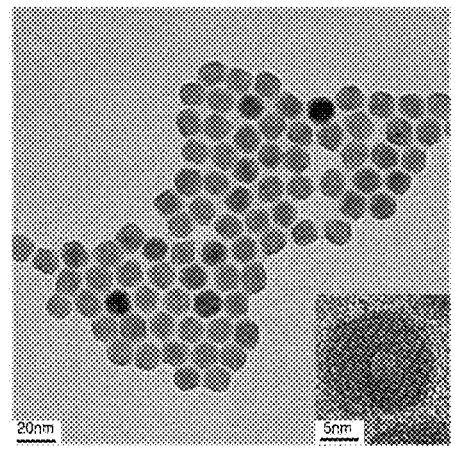
FIG. 5 shows a transmission electron microscopic image of a nanophosphor having a core/first shell structure according to an embodiment.

Referring to the X-ray diffraction pattern of FIG. 2, it was confirmed that the synthesized nanophosphor according to Comparative Example 1 did not have a tetragonal structure, but have an orthorhombic-based $GdF_3$ structure. This result shows that the nanophosphor having a $LiGdF_4$ structure, which was the target product, was not synthesized. However, referring to the X-ray diffraction pattern of FIG. 3, it was confirmed that the synthesized nanophosphor having the core and the synthesized nanophosphor having the core/first shell structure each have a tetragonal structure. This result shows that $LiGdF_4$ crystal has been formed well. Referring to FIG. 4, which shows the transmission electron microscopic image of the core nanoparticle synthesized according to Example 1, it was confirmed that the formed core nanoparticle was uniform and had a small particle size of 20 nm or less. Referring to FIG. 5, which shows the transmission electron microscopic image of the nanophosphor having a core/first shell structure, it was confirmed that the formed core nanoparticle had a uniform particle size and shape. Referring to the high-resolution transmission electron microscopic image on the bottom right side of FIG. 5, it was confirmed that a shell was epitaxially grown on the core.

<Example 3> Preparation of Green Emitting Up-Conversion Nanophosphor Having Core/First Shell/Second Shell Structure A nanophosphor having a core/first shell/second shell structure was prepared by using the $LiY_{0.2}F_4:Yb^{3+}_{0.8}/LiGdF_4:Yb^{3+}_{0.25},Tm^{3+}_{0.01}$ nanoparticle prepared according to Example 2, as a core, and a $LiGdF_4:Tb^{3+}$ compound.

0.85 mmol gadolinium chloride hexahydrate ($GdCl_3 \cdot 6H_2O$) and 0.15 mmol terbium chloride hexahydrate ($TbCl_3 \cdot 6H_2O$) were mixed with a solution including an oleic acid and 1-octadecene, and the resultant mixture was heat-treated at a temperature of 150° C. for 30 minutes to prepare a mixed solution including a lanthanide complex compound (step of preparing a first mixed solution).

The first mixed solution was mixed with a solution including the $LiY_{0.2}F_4:Yb^{3+}_{0.8}/LiGdF_4:Yb^{3+}_{0.25},Tm^{3+}_{0.01}$ nanoparticle prepared according to Example 2 to prepare a second mixed solution.

10 ml of a methanol solution including 2.5 mmol lithium hydroxide and 4 mmol ammonium fluoride was prepared (step of preparing a third mixed solution), and then mixed with the second mixed solution including the lanthanide complex compound (step of preparing a reaction solution).

The resultant mixed solution was sufficiently mixed, and then, methanol was removed therefrom, followed by heat-treatment in inert gas atmosphere. In this regard, when the heat-treatment temperature is less than 200° C., single tetragonal nanocrystals are not completely formed, and thus, the formed phosphor may not have strong emission characteristics; and when the heat-treatment temperature exceeds 370° C., over-reaction may occur, and thus, particles may agglomerate together to form larger particles, and the size distribution of formed particles is not uniform, leading to low luminance. Accordingly, the heat-treatment temperature was controlled to be in a range of 200 to 370° C., and the heat-treatment time was controlled to be in a range of 10 minutes to 4 hours (step of forming a nanoparticle). After the heat-treatment, the result was cooled to room temperature, thereby producing nanophosphor in the colloid state, having a particle diameter of 1 nm to 50 nm. The nanophosphor was washed with acetone or ethanol, and then, for storage purpose, dispersed in a non-polar solvent, for example, hexane, toluene, chloroform, or like.

Figure 6:
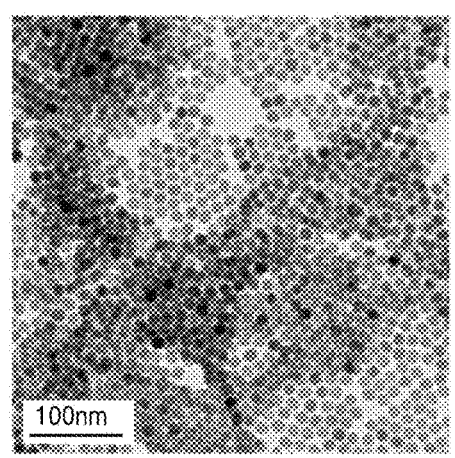
FIG. 6 shows a transmission electron microscopic image of a nanophosphor having a core/first shell/second shell structure according to an embodiment.

FIG. 6 shows a transmission electron microscopic image of an up-conversion nanophosphor having the core/first shell/second shell structure prepared according to Example 3. Referring to the transmission electron microscopic image, it was confirmed that a second shell was formed around the core/first shell, thereby resulting in a greater particle size.

<Example 4> Preparation of Green Emitting Up-Conversion Nanophosphor Having Core/First Shell/Second Shell/Third Shell Structure A nanophosphor having a core/first shell/second shell/third shell structure was prepared by using the $LiY_{0.2}F_4$:$Yb^{3+}_{0.8}$/$LiGdF_4$:$Yb^{3+}_{0.25}$,$Tm^{3+}_{0.01}$/$LiGdF_4$:$Tb^{3+}_{0.15}$ nanoparticle prepared according to Example 3, as a core, and a $LiYF_4$ compound.

1 mmol yttrium chloride hexahydrate ($YCl_3.6H_2O$) was mixed with a solution including an oleic acid and 1-octadecene, and the resultant mixture was heat-treated at a temperature of 150° C. for 30 minutes to prepare a mixed solution including a yttrium complex compound (step of preparing a first mixed solution).

The first mixed solution was mixed with a solution including the $LiY_{0.2}F_4$:$Yb^{3+}_{0.8}$/$LiGdF_4$:$Yb^{3+}_{0.25}$,$Tm^{3+}_{0.01}$/$LiGdF_4$:$Tb^{3+}_{0.15}$ nanoparticle prepared according to Example 3 to prepare a second mixed solution.

10 ml of a methanol solution including 2.5 mmol lithium hydroxide and 4 mmol ammonium fluoride was prepared (step of preparing a third mixed solution), and then mixed with the second mixed solution including the yttrium complex compound (step of preparing a reaction solution).

The resultant mixed solution was sufficiently mixed, and then, methanol was removed therefrom, followed by heat-treatment in inert gas atmosphere. In this regard, when the heat-treatment temperature is less than 200° C., single tetragonal nanocrystals are not completely formed, and thus, the formed phosphor may not have strong emission characteristics; and when the heat-treatment temperature exceeds 370° C., over-reaction may occur, and thus, particles may agglomerate together to form larger particles, and the size distribution of formed particles is not uniform, leading to low luminance. Accordingly, the heat-treatment temperature was controlled to be in a range of 200 to 370° C., and the heat-treatment time was controlled to be in a range of 10 minutes to 4 hours (step of forming a nanoparticle). After the heat-treatment, the result was cooled to room temperature, thereby producing nanophosphor in the colloid state, having a particle diameter of 1 nm to 70 nm. The nanophosphor was washed with acetone or ethanol, and then, for storage purpose, dispersed in a non-polar solvent, for example, hexane, toluene, chloroform, or like.

Figure 7:
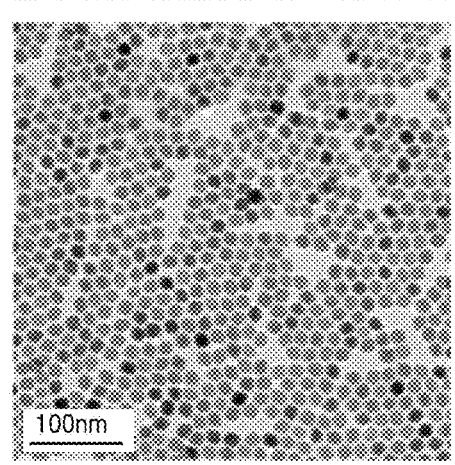
FIG. 7 shows a transmission electron microscopic image of a nanophosphor having a core/first shell/second shell/third shell structure according to an embodiment.
Figure 8:
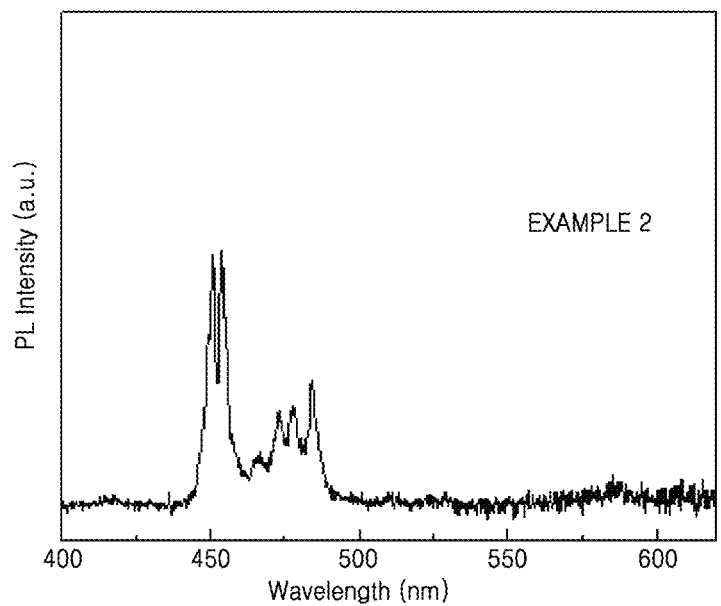
FIG. 8 shows an up-conversion emission spectrum of a nanophosphor having a core/first shell structure according to an embodiment.
Figure 9:
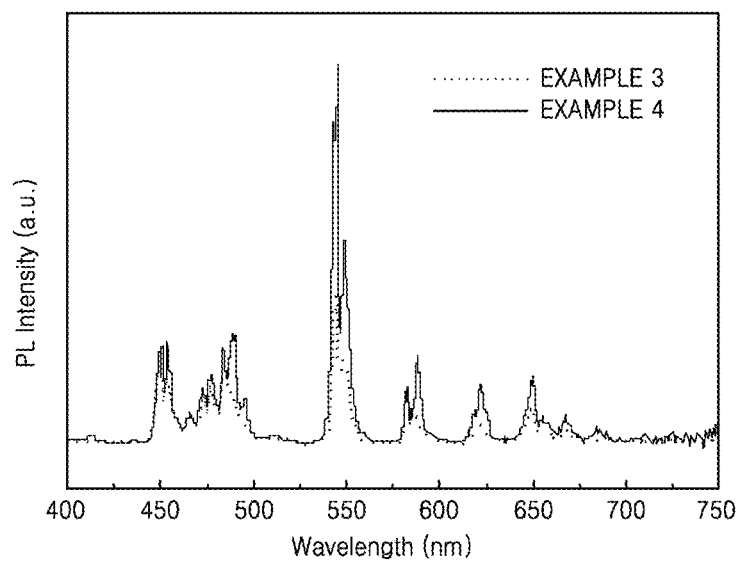
FIG. 9 shows an up-conversion emission spectra of a nanophosphor having a core/first shell/second shell structure prepared according to Example 3 and a nanophosphor having a core/first shell/second shell/third shell structure prepared according to Example 4.

FIG. 7 shows a transmission electron microscopic image of an up-conversion nanophosphor having a core/first shell/second shell/third shell structure prepared according to Example 4. Referring to FIG. 7, it was confirmed that a third shell was formed around the core/first shell/second shell, thereby resulting in a greater particle size. Referring to the emission spectrum of FIG. 8, the nanophosphor having the core/first shell structure synthesized according to Example 2 had its emission peak in the blue spectrum region. Referring to the emission spectrum of FIG. 9, the nanophosphor having the core/first shell/second shell structure synthesized according to Example 3 had its emission peak in the green spectrum region. Also, it was confirmed that, due to the formation of the additional shell around the core/first shell/second shell, the nanophosphor having the core/first shell/second shell/third shell structure prepared according to Example 4 had much stronger emission intensity in the green spectrum region than the core/first shell/second shell structure synthesized according to Example 3.

<Example 5> Preparation of Red Emitting Up-Conversion Nanophosphor Having Core/First Shell/Second Shell Structure A nanophosphor having a core/first shell/second shell structure was prepared by using the $LiY_{0.2}F_4$:$Yb^{3+}_{0.8}$/$LiGdF_4$:$Yb^{3+}_{0.25}$,$Tm^{3+}_{0.01}$ nanoparticle prepared according to Example 2, as a core, and a $LiGdF_4$:$Eu^{3+}$ compound. 0.85 mmol gadolinium chloride hexahydrate ($GdCl_3.6H_2O$) and 0.15 mmol europium chloride hexahydrate ($EuCl_3.6H_2O$) were mixed with a solution including an oleic acid and 1-octadecene, and the resultant mixture was heat-treated at a temperature of 150° C. for 30 minutes to prepare a mixed solution including a lanthanide complex compound (step of preparing a first mixed solution).

The first mixed solution was mixed with a solution including the $LiY_{0.2}F_4$:$Yb^{3+}_{0.8}$/$LiGdF_4$:$Yb^{3+}_{0.25}$,$Tm^{3+}_{0.01}$ nanoparticle prepared according to Example 2 to prepare a second mixed solution.

10 ml of a methanol solution including 2.5 mmol lithium hydroxide and 4 mmol ammonium fluoride was prepared (step of preparing a third mixed solution), and then mixed with the second mixed solution including the lanthanide complex compound (step of preparing a reaction solution).

The resultant mixed solution was sufficiently mixed, and then, methanol was removed therefrom, followed by heat-treatment in inert gas atmosphere. In this regard, when the heat-treatment temperature is less than 200° C., single tetragonal nanocrystals are not completely formed, and thus, the formed phosphor may not have strong emission characteristics; and when the heat-treatment temperature exceeds 370° C., over-reaction may occur, and thus, particles may agglomerate together to form larger particles, and the size distribution of formed particles is not uniform, leading to low luminance. Accordingly, the heat-treatment temperature was controlled to be in a range of 200 to 370° C., and the heat-treatment time was controlled to be in a range of 10 minutes to 4 hours (step of forming a nanoparticle). After the heat-treatment, the result was cooled to room temperature, thereby producing nanophosphor in the colloid state, having a particle diameter of 1 nm to 50 nm. The nanophosphor was washed with acetone or ethanol, and then, for storage purpose, dispersed in a non-polar solvent, for example, hexane, toluene, chloroform, or like.

Figure 10:
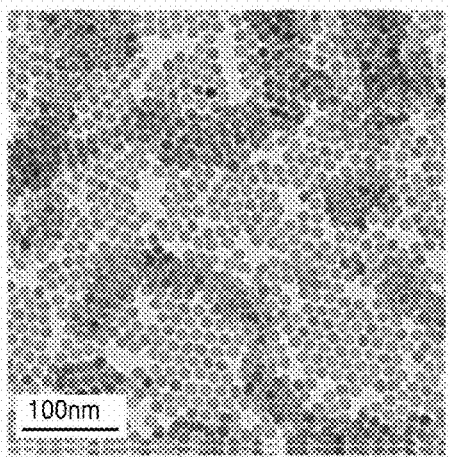
FIG. 10 shows a transmission electron microscopic image of a nanophosphor having a core/first shell/second shell structure according to an embodiment.

FIG. 10 shows a transmission electron microscopic image of an up-conversion nanophosphor having a core/first shell/second shell structure prepared according to Example 5. Referring to FIG. 10, it was confirmed that a second shell was formed around the core/first shell, thereby resulting in a greater particle size.

<Example 6> Preparation of Red Emitting Up-Conversion Nanophosphor Having Core/First Shell/Second Shell/Third Shell Structure A nanophosphor having a core/first shell/second shell/third shell structure was prepared by using the $LiY_{0.2}F_4$:$Yb^{3+}_{0.8}$/$LiGdF_4$:$Yb^{3+}_{0.25}$,$Tm^{3+}_{0.01}$/$LiGdF_4$:$Eu^{3+}_{0.15}$ nanoparticle prepared according to Example 5, as a core, and a $LiYF_4$ compound.

1 mmol yttrium chloride hexahydrate ($YCl_3.6H_2O$) was mixed with a solution including an oleic acid and 1-octadecene, and the resultant mixture was heat-treated at a temperature of 150° C. for 30 minutes to prepare a mixed solution including a yttrium complex compound (step of preparing a first mixed solution).

The first mixed solution was mixed with a solution including the $LiY_{0.2}F_4$:$Yb^{3+}_{0.8}$/$LiGdF_4$:$Yb^{3+}_{0.25}$,$Tm^{3+}_{0.01}$/$LiGdF_4$:$Eu^{3+}_{0.15}$ nanoparticle prepared according to Example 3 to prepare a second mixed solution.

10 ml of a methanol solution including 2.5 mmol lithium hydroxide and 4 mmol ammonium fluoride was prepared (step of preparing a third mixed solution), and then mixed with the second mixed solution including the yttrium complex compound (step of preparing a reaction solution).

The resultant mixed solution was sufficiently mixed, and then, methanol was removed therefrom, followed by heat-treatment in inert gas atmosphere. In this regard, when the heat-treatment temperature is less than 200° C., single tetragonal nanocrystals are not completely formed, and thus, the formed phosphor may not have strong emission characteristics; and when the heat-treatment temperature exceeds 370° C., over-reaction may occur, and thus, particles may agglomerate together to form larger particles, and the size distribution of formed particles is not uniform, leading to low luminance. Accordingly, the heat-treatment temperature was controlled to be in a range of 200 to 370° C., and the heat-treatment time was controlled to be in a range of 10 minutes to 4 hours (step of forming a nanoparticle). After the heat-treatment, the result was cooled to room temperature, thereby producing nanophosphor in the colloid state, having a particle diameter of 1 nm to 70 nm. The nanophosphor was washed with acetone or ethanol, and then, for storage purpose, dispersed in a non-polar solvent, for example, hexane, toluene, chloroform, or like.

Figure 11:
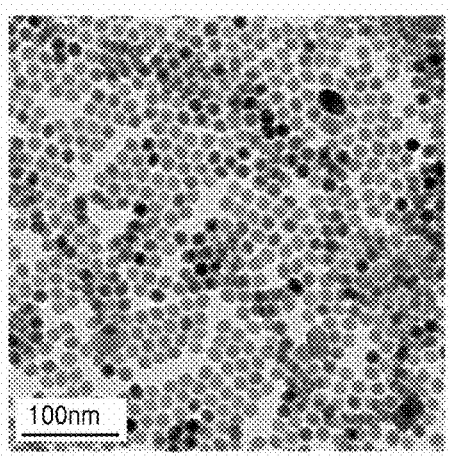
FIG. 11 shows a transmission electron microscopic image of a nanophosphor having a core/first shell/second shell/third shell structure according to an embodiment.
Figure 12:
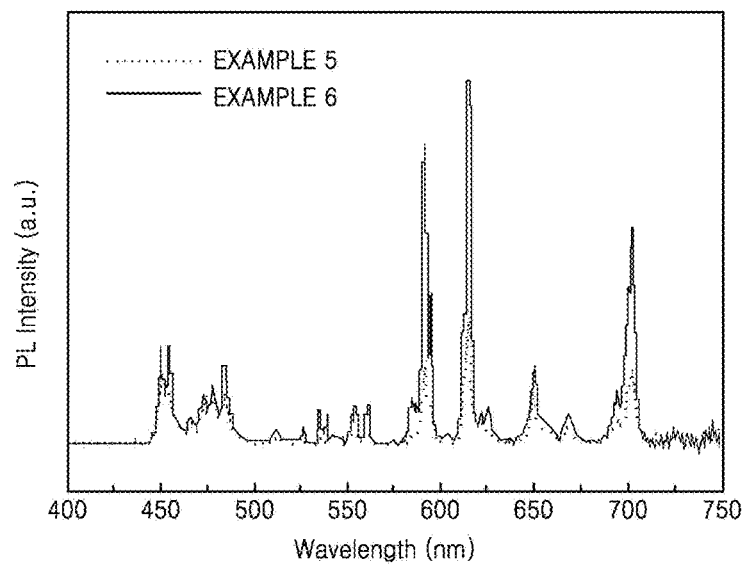
FIG. 12 shows up-conversion emission spectra of a nanophosphor having a core/first shell/second shell structure prepared according to Example 5 and a nanophosphor having a core/first shell/second shell/third shell structure prepared according to Example 6.

FIG. 11 shows a transmission electron microscopic image of an up-conversion nanophosphor having a core/first shell/second shell/third shell structure prepared according to Example 6. Referring to FIG. 11, it was confirmed that a third shell was formed around the core/first shell/second shell, thereby resulting in a greater particle size. Referring to the emission spectrum of FIG. 12, the core/first shell/second shell structure synthesized according to Example 5 had its emission peak in the red spectrum region. Also, it was confirmed that, due to the formation of the additional shell around the core/first shell/second shell, the nanophosphor having the core/first shell/second shell/third shell structure prepared according to Example 6 had much stronger emission intensity in the red spectrum region than the core/first shell/second shell structure synthesized according to Example 5.

<Example 7> Preparation of White Emitting Up-Conversion Nanophosphor Having Core/First Shell/Second Shell Structure A nanophosphor having a core/first shell/second shell structure was prepared by using the $LiY_{0.2}F_4:Yb^{3+}_{0.8}/LiGdF_4:Yb^{3+}_{0.25},Tm^{3+}_{0.01}$ nanoparticle prepared according to Example 2, as a core, and a $LiGdF_4:Tb^{3+},Eu^{3+}$ compound.

0.83 mmol gadolinium chloride hexahydrate ($GdCl_3.6H_2O$), 0.15 mmol terbium chloride hexahydrate ($TbCl_3.6H_2O$), and 0.02 mmol europium chloride hexahydrate ($EuCl_3.6H_2O$) were mixed with a solution including an oleic acid and 1-octadecene, and the resultant mixture was heat-treated at a temperature of 150° C. for 30 minutes to prepare a mixed solution including a lanthanide complex compound (step of preparing a first mixed solution).

The first mixed solution was mixed with a solution including the $LiY_{0.2}F_4:Yb^{3+}_{0.8}/LiGdF_4:Yb^{3+}_{0.25},Tm^{3+}_{0.01}$ nanoparticle prepared according to Example 2 to prepare a second mixed solution.

10 ml of a methanol solution including 2.5 mmol lithium hydroxide and 4 mmol ammonium fluoride was prepared (step of preparing a third mixed solution), and then mixed with the second mixed solution including the lanthanide complex compound (step of preparing a reaction solution).

The resultant mixed solution was sufficiently mixed, and then, methanol was removed therefrom, followed by heat-treatment in inert gas atmosphere. In this regard, when the heat-treatment temperature is less than 200° C., single tetragonal nanocrystals are not completely formed, and thus, the formed phosphor may not have strong emission characteristics; and when the heat-treatment temperature exceeds 370° C., over-reaction may occur, and thus, particles may agglomerate together to form larger particles, and the size distribution of formed particles is not uniform, leading to low luminance. Accordingly, the heat-treatment temperature was controlled to be in a range of 200 to 370° C., and the heat-treatment time was controlled to be in a range of 10 minutes to 4 hours (step of forming a nanoparticle). After the heat-treatment, the result was cooled to room temperature, thereby producing nanophosphor in the colloid state, having a particle diameter of 1 nm to 50 nm. The nanophosphor was washed with acetone or ethanol, and then, for storage purpose, dispersed in a non-polar solvent, for example, hexane, toluene, chloroform, or like.

Figure 13:
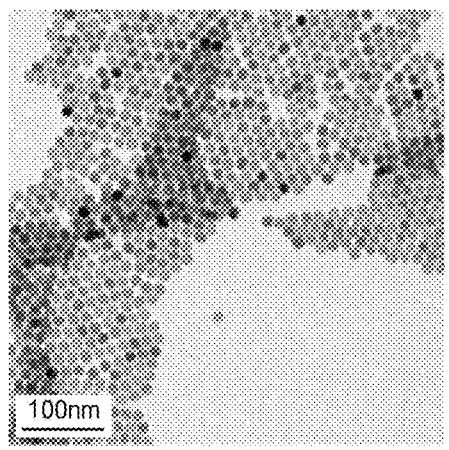
FIG. 13 shows a transmission electron microscopic image of a nanophosphor having a core/first shell/second shell structure according to an embodiment.

FIG. 13 shows a transmission electron microscopic image of an up-conversion nanophosphor having a core/first shell/second shell structure prepared according to Example 7. Referring to FIG. 7, it was confirmed that a second shell was formed around the core/first shell, thereby resulting in a greater particle size.

<Example 8> Preparation of White Emitting Up-Conversion Nanophosphor Having Core/First Shell/Second Shell/Third Shell Structure A nanophosphor having a core/first shell/second shell/third shell structure was prepared by using the $LiY_{0.2}F_4:Yb^{3+}_{0.8}/LiGdF_4:Yb^{3+}_{0.25}, Tm^{3+}_{0.01}/LiGdF_4:Tb^{3+}_{0.15},Eu^{3+}_{0.02}$ nanoparticle prepared according to Example 7, as a core, and a $LiYF_4$ compound.

1 mmol yttrium chloride hexahydrate ($YCl_3.6H_2O$) was mixed with a solution including an oleic acid and 1-octadecene, and the resultant mixture was heat-treated at a temperature of 150° C. for 30 minutes to prepare a mixed solution including a yttrium complex compound (step of preparing a first mixed solution).

The first mixed solution was mixed with a solution including the $LiY_{0.2}F_4:Yb^{3+}_{0.8}/LiGdF_4:Yb^{3+}_{0.25}, Tm^{3+}_{0.01}/LiGdF_4:Tb^{3+}_{0.15},Eu^{3+}_{0.02}$ nanoparticle prepared according to Example 7 to prepare a second mixed solution.

10 ml of a methanol solution including 2.5 mmol lithium hydroxide and 4 mmol ammonium fluoride was prepared (step of preparing a third mixed solution), and then mixed with the second mixed solution including the yttrium complex compound (step of preparing a reaction solution).

The resultant mixed solution was sufficiently mixed, and then, methanol was removed therefrom, followed by heat-treatment in inert gas atmosphere. In this regard, when the heat-treatment temperature is less than 200° C., single tetragonal nanocrystals are not completely formed, and thus, the formed phosphor may not have strong emission characteristics; and when the heat-treatment temperature exceeds 370° C., over-reaction may occur, and thus, particles may agglomerate together to form larger particles, and the size distribution of formed particles is not uniform, leading to low luminance. Accordingly, the heat-treatment temperature was controlled to be in a range of 200 to 370° C., and the heat-treatment time was controlled to be in a range of 10 minutes to 4 hours (step of forming a nanoparticle). After the heat-treatment, the result was cooled to room temperature, thereby producing nanophosphor in the colloid state, having a particle diameter of 1 nm to 70 nm. The nanophosphor was washed with acetone or ethanol, and then, for storage purpose, dispersed in a non-polar solvent, for example, hexane, toluene, chloroform, or like.

Figure 14:
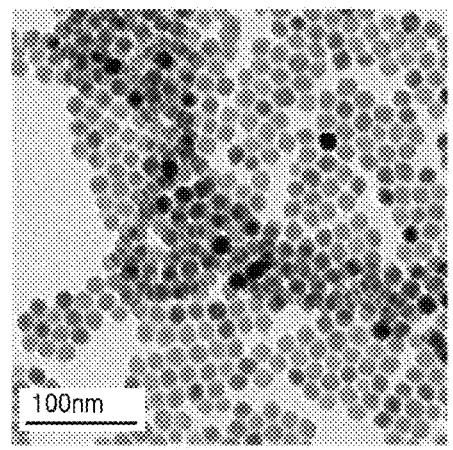
FIG. 14 shows a transmission electron microscopic image of a nanophosphor having a core/first shell/second shell/third shell structure according to an embodiment.
Figure 15:
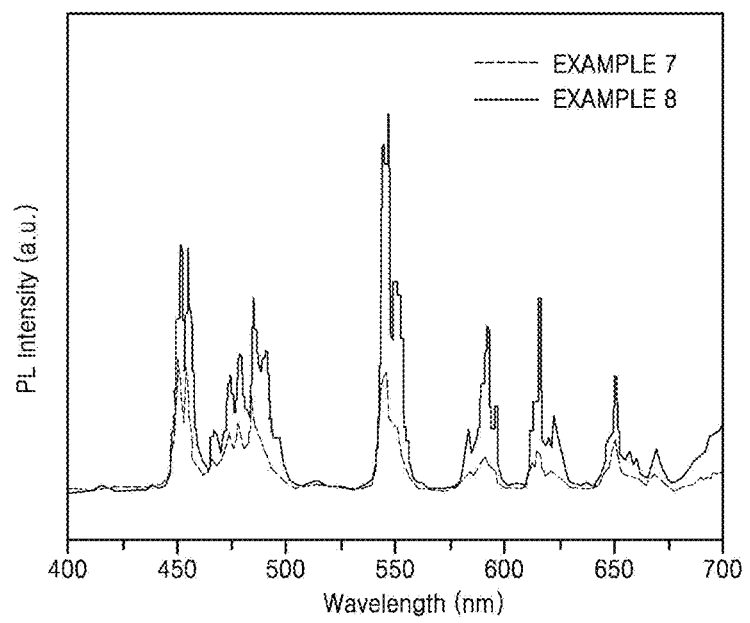
FIG. 15 shows up-conversion emission spectra of a nanophosphor having a core/first shell/second shell structure prepared according to Example 7 and a nanophosphor having a core/first shell/second shell/third shell structure prepared according to Example 8.

FIG. 14 shows a transmission electron microscopic image of an up-conversion nanophosphor having a core/first shell/second shell/third shell structure prepared according to Example 8. Referring to FIG. 14, it was confirmed that a third shell was formed around the core/first shell/second shell, thereby resulting in a greater particle size. Referring to the emission spectrum of FIG. 15, the core/first shell/second shell structure synthesized according to Example 7 had its emission peaks in blue, green, and red spectrum regions. Also, it was confirmed that, due to the formation of the additional shell around the core/first shell/second shell, the nanophosphor having the core/first shell/second shell/third shell structure prepared according to Example 8 had much stronger emission intensity in the blue, green, and red spectrum regions than the core/first shell/second shell structure synthesized according to Example 7. As a result, as shown in the emission image of FIG. 16, it was confirmed that white light was emitted by the solution of the up-conversion nanophosphor having the core/first shell/second shell/third shell structure prepared according to Example 8.

<Example 9> Preparation of Blue Emitting Up-Conversion Nanophosphor Having Core/First Shell/Second Shell Structure A nanophosphor having a core/first shell/second shell structure was prepared by using the $LiY_{0.2}F_4:Yb^{3+}_{0.8}/LiGdF_4:Yb^{3+}_{0.25},Tm^{3+}_{0.01}$ nanoparticle prepared according to Example 2, as a core, and a $LiYF_4$ compound.

1 mmol yttrium chloride hexahydrate ($YCl_3.6H_2O$) was mixed with a solution including an oleic acid and 1-octadecene, and the resultant mixture was heat-treated at a temperature of 150° C. for 30 minutes to prepare a mixed solution including a yttrium complex compound (step of preparing a first mixed solution).

The first mixed solution was mixed with a solution including the $LiY_{0.2}F_4:Yb^{3+}_{0.8}/LiGdF_4:Yb^{3+}_{0.25},Tm^{3+}_{0.01}$ nanoparticle prepared according to Example 2 to prepare a second mixed solution.

10 ml of a methanol solution including 2.5 mmol lithium hydroxide and 4 mmol ammonium fluoride was prepared (step of preparing a third mixed solution), and then mixed with the second mixed solution including the yttrium complex compound (step of preparing a reaction solution).

The resultant mixed solution was sufficiently mixed, and then, methanol was removed therefrom, followed by heat-treatment in inert gas atmosphere. In this regard, when the heat-treatment temperature is less than 200° C., a single tetragonal nanocrystal is not completely formed, and thus, the formed phosphor may not have strong emission characteristics; and when the heat-treatment temperature exceeds 370° C., over-reaction may occur, and thus, particles may agglomerate together to form larger particles, and the size distribution of formed particles is not uniform, leading to low luminance. Accordingly, the heat-treatment temperature was controlled to be in a range of 200 to 370° C., and the heat-treatment time was controlled to be in a range of 10 minutes to 4 hours (step of forming a nanoparticle). After the heat-treatment, the result was cooled to room temperature, thereby producing nanophosphor in the colloid state, having a particle diameter of 1 nm to 50 nm. The nanophosphor was washed with acetone or ethanol, and then, for storage purpose, dispersed in a non-polar solvent, for example, hexane, toluene, chloroform, or like.

Figure 16:
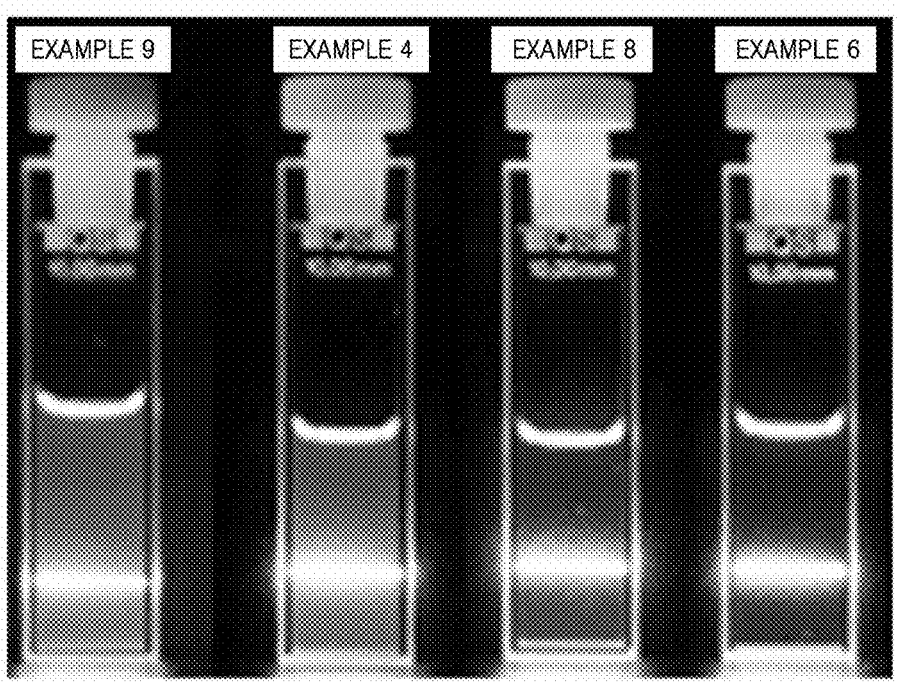
FIG. 16 shows up-conversion emission images of solutions of a nanophosphor having a core/first shell/second shell structure and nanophosphors having a core/first shell/second shell/third shell structure.

As shown in the emission image of FIG. 16, it was confirmed that blue light was emitted by the solution of the up-conversion nanophosphor having the core/first shell/second shell structure prepared according to Example 9. It was also confirmed that bright green and red light was emitted by the solutions of the up-conversion nanophosphors of the core/first shell/second shell/third shell structures synthesized according to Example 4 and Example 6. This result shows that various emission colors including red, green, blue, and white can be embodied by adjusting the shell composition of an up-conversion nanophosphor having a core/first shell/second shell/third shell structure.

<Example 10> Preparation of Silica Composite Including Red Emitting Up-Conversion Nanophosphor Having Core/First Shell/Second Shell/Third Shell Structure A silica composite including the $LiY_{0.2}F_4:Yb^{3+}_{0.8}/LiGdF_4:Yb^{3+}_{0.25},Tm^{3+}_{0.01}/LiGdF_4:Eu^{3+}_{0.15}/LiYF_4$ nanoparticle prepared according to Example 6 was prepared 1.00 ml of a solution of the red emission up-conversion nanophosphor having the core/first shell/second shell/third shell structure prepared according to Example 6 was added to 2.00 ml of a perhydropolysilazane solution (Samsung SDI model number: CISD-15001, 18.6 wt % dibutyl ether solution), and then, annealed at room temperature in the atmosphere condition for 24 hours. The obtained product was milled by using a mortar and a pestle, and then, dried at a temperature of 60° C. for 7 hours and 30 minutes to prepare an up-conversion nanophosphor-silica composite.

This experiment has been explained in connection with the nanophosphor having the core/first shell/second shell/third shell structure. However, the nanophosphor according to the inventive concept is not limited thereto, and various other examples of the nanophosphor are also applicable herein. For example, the nanophosphor according to the inventive concept may have the core/first shell structure alone, the core/first shell/second shell structure alone, or the core/first shell/third shell structure alone.

An inorganic nanophosphor having the core/first shell/second shell/third shell structure according to embodiments of the present disclosure shows up-conversion emission having emission peaks in blue, green, and red wavelength regions corresponding to Tm, Tb, and Eu, has increased up-conversion emission intensity due to the formation of a shell on the outermost shell, enabling color-tunable high luminance up-conversion emission, and has white light emission characteristics in addition to mono-color light emission characteristics.

An inorganic nanophosphor according to embodiments of the present disclosure uses up-conversion emission. Accordingly, the inorganic nanophosphor can be used as contrast media for bio imaging, and also used in disease diagnosis fields. Various wavelength regions of emission may contribute to accuracy of fluorescent imaging. Also, due to the strong up-conversion emission from the core/first shell/second shell/third shell structure, the inorganic nanophosphor can be used as a sensor that detects infrared light that is not detectable by the human eye.

The increased efficiency of light emission characteristics may lead to a greater level of sensitivity of an infrared-ray sensor. The conversion of the infrared light, which is not used in a solar cell, into visible light may result in a greater efficiency of the solar cell.

The up-conversion nanophosphor having the core and core/first shell/second shell/third shell structure according to embodiments of the present disclosure uses infrared light that is not detectable by the human eye. Accordingly, the up-conversion nanophosphor can be used in security-related fields, for example, in a counterfeit prevention code. Since particles of the up-conversion nanophosphor have a size of 50 nm or less, it is difficult to detect the up-conversion nanophosphor. Also, since the up-conversion nanophosphor can show an emission characteristic that is not obtainable from bulk powder phosphor, it can be used in high-grade security code. Due to the uniform and small size thereof, a transparent polymer composite can be manufactured, and since the manufactured polymer composite can emit various wavelengths of color, it can be applied in a transparent display device.

The up-conversion nanophosphor can emit white light. In this case, the up-conversion nanophosphor can be used in, for example, an illuminating device using infrared light. However, these effects thereof are an example only, and do not limit the scope of the inventive concept.

As described above, the inventive concept has been described in connection with example embodiments. However, it is obvious to one of ordinary skill in the art that the embodiments described above may be modified or changed in various manners as long as within the inventive concept or region recited in the following claims.

One of ordinary skill in the art may improve or change the inventive concept in various manners, and as long as being obvious to one of ordinary skill in the art, the improvement and change may be within the claimed scope of the inventive concept.

What is claimed is:

1. An up-conversion nanophosphor comprising:
a core comprising a $Yb^{3+}$-doped fluoride-based nanoparticle represented by $LiY_{1-x-y}L_yF_4:Yb^{3+}_x$, where, x and y are real numbers, and $0 \leq x \leq 1$, $0 \leq y \leq 1$, and $0 \leq x+y \leq 1$, and L is any one selected from Y, Dy, Ho, Er, Tm, Lu, and a combination thereof;
a first shell comprising a fluoride-based crystalline compound that is co-doped with at least one selected from $Yb^{3+}$ and $Tm^{3+}$, the fluoride-based crystalline compound surrounding at least a portion of the core, and represented by $LiGd_{1-p-q-r}M_rF_4:Yb^{3+}_p,Tm^{3+}_q$, where, p, q and r are real numbers, and $0<p \leq 0.5$, $0<q \leq 0.2$, $0 \leq r \leq 1$, and $0<p+q+r<1$, and M is any one selected from a first rare-earth element and a combination thereof, wherein the first rare-earth element comprises any one selected from Gd, Y, La, Ce, Pr, Nd, Pm, Sm, Eu, Tb, Dy, Ho, Er, and Lu; and
a second shell that is a fluoride-based emission shell comprising a compound surrounding at least a portion of the first shell, and represented by $LiGd_{1-s-t-u}N_uF_4:Tb^{3+}_s, Eu^{3+}_t$ where, s, t and u are real numbers, and $0 \leq s \leq 0.5$, $0<t \leq 0.5$, $0 \leq u \leq 1$, and $0<s+t+u<1$, and N is any one selected from a second rare-earth element and a combination thereof, wherein the second rare-earth element comprises any one selected from Gd, Y, La, Ce, Pr, Nd, Pm, Sm, Dy, Ho, Er, Tm, Yb, and Lu.

2. The up-conversion nanophosphor of claim 1, further comprising:
a second shell that is a fluoride-based emission shell including a compound represented by Formula 3, and surrounds at least a portion of the first shell; and
a third shell that is a crystalline shell including a compound represented by Formula 4, and surrounds at least a portion of the second shell:

$$LiGd_{1-s-t-u}N_uF_4:Tb^{3+}_s,Eu^{3+}_t \qquad \text{[Formula 3]}$$

wherein, in Formula 3, s satisfies the condition of $0<s \leq 0.5$ and is a real number, t satisfies the condition of $0<t \leq 0.5$ and is a real number, u satisfies the condition of $0 \leq u \leq 1$ and is a real number, u is any real number that satisfies the condition of $0<s+t+u<1$, and N is any one selected from a second rare-earth element and a combination thereof, wherein the second rare-earth element comprises any one selected from Gd, Y, La, Ce, Pr, Nd, Pm, Sm, Dy, Ho, Er, Tm, Yb, and Lu, and $$LiY_{1-v}O_vF_4, \qquad \text{[Formula 4]}$$

wherein, in Formula 4, v satisfies the condition of $0 \leq v \leq 1$ and is a real number, and O is any one selected from a third rare-earth element and a combination thereof, wherein the third rare-earth element comprises any one selected from Y, La, Ce, Pr, Nd, Pm, Sm, Eu, Gd, Tb, Dy, Ho, Er, Tm, Yb, and Lu.

3. The up-conversion nanophosphor of claim 1, wherein a third shell that is a crystalline shell including a compound represented by Formula 4, and surrounds at least a portion of the first shell:

$$LiY_{1-v}O_vF_4 \qquad \text{[Formula 4]}$$

wherein, in Formula 4, v satisfies the condition of $0 \leq v \leq 1$ and is a real number, and O is any one selected from a third rare-earth element and a combination thereof, wherein the third rare-earth element comprises any one selected from Y, La, Ce, Pr, Nd, Pm, Sm, Eu, Gd, Tb, Dy, Ho, Er, Tm, Yb, and Lu.

4. The up-conversion nanophosphor of claim 1, wherein the $Yb^{3+}$-doped fluoride-based nanoparticle has a tetragonal structure, and the core has a size of about 1 nm to about 40 nm.

5. The up-conversion nanophosphor of claim 1, wherein the up-conversion nanophosphor has a size of about 2 nm to about 50 nm.

6. The up-conversion nanophosphor of claim 2, wherein the up-conversion nanophosphor has a size of about 2 nm to about 70 nm.

7. A silica composite comprising:
a core comprising a $Yb^{3+}$-doped fluoride-based nanoparticle represented by $LiY_{1-x-y}L_yF_4:Yb^{3+}_x$, where, x and y are real numbers, and $0 \leq x \leq 1$, $0 \leq y \leq 1$, and $0 \leq x+y \leq 1$, and L is any one selected from Y, Dy, Ho, Er, Tm, Lu, and a combination thereof;
a first shell comprising a fluoride-based crystalline compound that is co-doped with at least one selected from $Yb^{3+}$ and $Tm^{3+}$, the fluoride-based crystalline compound surrounding at least a portion of the core, and represented by $LiGd_{1-p-q-r}M_rF_4:Yb^{3+}_p, Tm^{3+}_q$, where, p, q and r are real numbers, and $0<p \leq 0.5$, $0<q \leq 0.2$, $0 \leq r \leq 1$, and $0<p+q+r<1$, and M is any one selected from a first rare-earth element and a combination thereof, wherein the first rare-earth element comprises any one selected from Gd, Y, La, Ce, Pr, Nd, Pm, Sm, Eu, Tb, Dy, Ho, Er, and Lu; and
a second shell that is a fluoride-based emission shell comprising a compound surrounding at least a portion of the first shell, and represented by $LiGd_{1-s-t-u}N_uF_4:Tb^{3+}_s, Eu^{3+}_t$ where, s, t and u are real numbers, and $0<s \leq 0.5$, $0<t \leq 0.5$, $0 \leq u \leq 1$, and $0<s+t+u<1$, and N is any one selected from a second rare-earth element and a combination thereof, wherein the second rare-earth element comprises any one selected from Gd, Y, La, Ce, Pr, Nd, Pm, Sm, Dy, Ho, Er, Tm, Yb, and Lu.

8. A display device comprising the up-conversion nanophosphor of claim 1.

9. A fluorescent contrast media comprising the up-conversion nanophosphor of claim 1.

10. A solar cell comprising the up-conversion nanophosphor of claim 1.

11. An anti-falsification code comprising the up-conversion nanophosphor of claim 1.

* * * * *